(12) United States Patent
Kuen et al.

(10) Patent No.: US 6,837,879 B2
(45) Date of Patent: Jan. 4, 2005

(54) CONTAINMENT FLAPS FOR ABSORBENT ARTICLE

(75) Inventors: David A. Kuen, Neenah, WI (US); Sherry A. Van Dyke, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 10/003,970

(22) Filed: Oct. 31, 2001

(65) Prior Publication Data

US 2003/0083636 A1 May 1, 2003

(51) Int. Cl.[7] .................................................. A61F 13/15
(52) U.S. Cl. .............. 604/385.28; 604/396; 604/385.24; 604/385.25
(58) Field of Search ....................... 604/385.28, 385.24, 604/385.25, 385.01, 396

(56) References Cited

U.S. PATENT DOCUMENTS

| | | |
|---|---|---|
| 4,695,278 A | 9/1987 | Lawson |
| 4,704,115 A | 11/1987 | Buell |
| 4,808,177 A | 2/1989 | DesMarais et al. |
| 4,909,803 A | 3/1990 | Aziz et al. |
| 4,938,753 A | 7/1990 | Van Gompel et al. |
| 5,085,654 A * | 2/1992 | Buell .......................... 604/370 |
| 5,192,606 A | 3/1993 | Proxmire et al. |
| 5,236,430 A | 8/1993 | Bridges |
| 5,358,500 A | 10/1994 | Lavon et al. |
| 5,383,871 A | 1/1995 | Carlin et al. |
| 5,405,342 A | 4/1995 | Roessler et al. |
| 5,458,591 A | 10/1995 | Roessler et al. |
| 5,476,457 A | 12/1995 | Roessler et al. |
| 5,520,673 A | 5/1996 | Yarbrough et al. |
| 5,562,650 A | 10/1996 | Everett et al. |
| 5,582,606 A | 12/1996 | Bruemmer et al. |
| 5,591,155 A * | 1/1997 | Nishikawa et al. .......... 604/393 |
| 5,593,399 A | 1/1997 | Tanzer et al. |
| 5,593,401 A | 1/1997 | Sosalla et al. |
| 5,613,959 A | 3/1997 | Roessler et al. |
| 5,624,426 A * | 4/1997 | Roe et al. .............. 604/385.28 |
| 5,649,918 A | 7/1997 | Schleinz |
| 5,649,919 A | 7/1997 | Roessler et al. |
| 5,669,896 A | 9/1997 | Kielpikowski |

(List continued on next page.)

FOREIGN PATENT DOCUMENTS

| | | |
|---|---|---|
| EP | 0 622 063 A2 | 11/1994 |
| EP | 0 433 951 B1 | 8/1996 |
| EP | 0 539 703 B1 | 3/1997 |
| EP | 0 627 210 B1 | 3/2000 |
| EP | 1 133 963 A2 | 9/2001 |

(List continued on next page.)

OTHER PUBLICATIONS

International Search Report for PCT/US 02/22855 dated May 23, 2003.

*Primary Examiner*—Jacqueline Stephens
(74) *Attorney, Agent, or Firm*—Senniger Powers (57) ABSTRACT

A disposable absorbent article for personal wear has an inner layer, an outer layer and an absorbent body disposed therebetween. Containment flaps are secured to the inner layer of the article, with each flap having a first layer extending outward from the inner layer of the article to a distal end of the flap. A generally liquid permeable second layer of the flap extends in opposed relation with a medial surface of the flap first layer of the flap and is free from fixed engagement therewith along at least a portion thereof whereby the flap second layer and the portion of the medial surface of the flap first layer define a surge chamber therebetween for receiving liquid body waste. The inner layer of the disposable article is interposed between the surge chamber and the absorbent body.

36 Claims, 5 Drawing Sheets

U.S. PATENT DOCUMENTS

| | | |
|---|---|---|
| 5,669,897 A | 9/1997 | Lavon et al. |
| 5,674,213 A | 10/1997 | Sauer |
| 5,676,661 A | 10/1997 | Faulks et al. |
| 5,683,531 A | 11/1997 | Roessler et al. |
| 5,695,488 A | 12/1997 | Sosalla |
| 5,704,928 A * | 1/1998 | Morita et al. .......... 604/385.23 |
| 5,752,947 A | 5/1998 | Awolin |
| 5,776,121 A | 7/1998 | Roe et al. |
| 5,776,122 A | 7/1998 | Faulks et al. |
| 5,814,035 A | 9/1998 | Gryskiewicz et al. |
| 5,843,067 A | 12/1998 | Trombetta et al. |
| 5,895,382 A | 4/1999 | Popp et al. |
| 5,899,894 A | 5/1999 | Palumbo et al. |
| 5,931,825 A | 8/1999 | Kuen et al. |
| 5,941,864 A | 8/1999 | Roe |
| 5,957,906 A | 9/1999 | Roe et al. |
| 5,977,430 A | 11/1999 | Roe et al. |
| 5,993,433 A | 11/1999 | St. Louis et al. |
| 6,017,336 A | 1/2000 | Sauer |
| 6,022,338 A | 2/2000 | Putzer |
| 6,066,121 A | 5/2000 | Lindquist et al. |
| 6,110,158 A | 8/2000 | Kielpikowski |
| 6,133,501 A | 10/2000 | Hallock et al. |
| 6,186,992 B1 | 2/2001 | Roe et al. |
| 6,186,996 B1 * | 2/2001 | Martin ................... 604/385.19 |
| 6,248,098 B1 | 6/2001 | Sayama |
| 6,293,934 B1 * | 9/2001 | Kumasaka ............. 604/385.27 |
| 6,547,773 B2 * | 4/2003 | Kleinschmidt et al. ................... 604/385.101 |
| 2002/0058920 A1 * | 5/2002 | Toyoda et al. ......... 604/385.28 |

FOREIGN PATENT DOCUMENTS

| | | |
|---|---|---|
| FR | 2 699 813 A1 | 7/1994 |
| JP | 02-065859 A2 | 3/1990 |
| JP | 02-156946 A2 | 6/1990 |
| JP | 02-174845 A2 | 7/1990 |
| JP | 03-121069 A2 | 5/1991 |
| JP | 03-165761 A2 | 7/1991 |
| JP | 03-218752 A2 | 9/1991 |
| JP | 03-286760 A2 | 12/1991 |
| JP | 04-150853 A2 | 5/1992 |
| JP | 04-200543 A2 | 7/1992 |
| JP | 04-218157 A2 | 8/1992 |
| JP | 04-325153 A2 | 11/1992 |
| JP | 05-293134 A2 | 11/1993 |
| JP | 05-293138 A2 | 11/1993 |
| JP | 07-184946 A2 | 7/1995 |
| JP | 07-184947 A2 | 7/1995 |
| JP | 07-184995 A2 | 7/1995 |
| WO | WO 95/15140 A1 | 6/1995 |
| WO | WO 96/03953 A1 | 2/1996 |
| WO | WO 97/17926 A1 | 5/1997 |
| WO | WO 97/20532 A1 | 6/1997 |
| WO | WO 97/21409 A1 | 6/1997 |
| WO | WO 97/31602 A1 | 9/1997 |
| WO | WO 97/31603 A1 | 9/1997 |

* cited by examiner

CONTAINMENT FLAPS FOR ABSORBENT ARTICLE

BACKGROUND OF THE INVENTION

The present invention relates to disposable absorbent articles, such as those used as personal care products, and more particularly to such a disposable absorbent article having containment flaps for improved containment of liquid body waste.

Disposable absorbent articles find widespread use as personal care products such as diapers, children's toilet training pants, adult incontinence garments, sanitary napkins and the like, as well as surgical bandages and sponges. These articles absorb and contain body waste and are intended to be discarded after a limited period of use; i.e., the articles are not intended to be laundered or otherwise restored for reuse. Conventional disposable absorbent articles comprise an absorbent body disposed between a liner adapted for contacting the wearer's skin and an outer cover for inhibiting liquid body waste absorbed by the absorbent body from leaking out of the article. The liner of the absorbent article is typically liquid permeable to permit liquid body waste to pass therethrough for absorption by the absorbent body.

Desired performance objectives of these disposable absorbent articles include little or no leakage from the article and a dry feel to the wearer. However, some available disposable absorbent articles may fail to inhibit leakage, even where the total absorbent capacity of the absorbent body is unrealized. Leakage can result from an insufficient rate of liquid body waste passing through the liner of the article or from an insufficient rate of absorption by the absorbent body, especially upon the occurrence of a second or even third surge of liquid body waste. For example, in diapers and children's training pants, a surge of urine flowing laterally outward toward opposite edges of the article may not penetrate through the liner of the article or be absorbed by the absorbent body at a rate sufficient to prevent some of the urine from leaking out between the wearer's skin and the opposite edges of the article.

One attempt to eliminate such leakage is the provision of a pair of longitudinally extending (e.g., front-to-back) containment flaps on the liner of the article. The containment flaps are typically spaced laterally from each other and positioned inward from the opposite edges of the article, particularly in the crotch area of diapers and training pants. For example, U.S. Pat. No. 5,895,382 discloses containment flaps for training pants in which the flaps each include a liquid permeable outer layer and a liquid impermeable inner layer. Elastic members are held between the outer and inner layers at the distal end of each flap to bias the flaps toward a generally upright position away from the liner of the article. The outer layer of the flap is folded over a small portion of the inner layer at the distal end of the flap to enclose the elastic members within the flap.

These containment flaps are intended to provide a barrier against the laterally outward flow of liquid body waste toward the edges of the article. In practice, however, leakage may still occur if a surge of liquid waste is released by the wearer because the absorbent article may not absorb the liquid at a rate sufficient to avoid substantial outward flow against the flaps, which may result in flow over the containment flaps and subsequent leakage from the edges of the article.

Therefore, despite the improved body waste containment obtained by providing conventional containment flaps, there continues to be a need for further improvements to inhibit leakage from disposable absorbent articles resulting from surges of liquid body waste rushing laterally outward over the containment flaps.

SUMMARY OF THE INVENTION

In general, a disposable absorbent article of the present invention comprises an inner layer adapted for contiguity with the wearer's skin, with at least a portion of the inner layer being liquid permeable. An outer layer is in opposed relation with the inner layer and an absorbent body is disposed between the inner layer and the outer layer of the article for absorbing liquid body waste. A pair of containment flaps is secured to the inner layer of the article in spaced relation with each other, with each flap having a base adjacent the inner layer of the article and a distal end. At least a portion of the distal end of the flap is movable relative to the base to a position in which the distal end is spaced from the inner layer of the article. The containment flaps each comprise a first layer extending from the base of the flap to the distal end of the flap. The flap first layer has a lateral surface and a medial surface. A generally liquid permeable second layer is in opposed relation with the medial surface of the flap first layer and is free from fixed engagement with at least a portion of the medial surface of the flap first layer to define a surge chamber therebetween for receiving body waste. The liquid permeable portion of the inner layer of the article is interposed between the surge chamber and the absorbent body of the article.

In another aspect of the present invention, the disposable absorbent article generally comprises an inner layer adapted for contiguity with the wearer's skin, with at least a portion of the inner layer being liquid permeable. An outer layer is in opposed relation with the inner layer of the article and an absorbent body is disposed between the inner layer and the outer layer of the article for absorbing liquid body waste. A pair of containment flaps is secured to the inner layer of the article in spaced relation with each other, with each flap having a base secured to the inner layer of the article and a distal end. At least a portion of the distal end of the flap is movable relative to the base to a position in which the distal end of the flap is spaced from the inner layer of the article. Each containment flap comprises a first layer extending from the base of the flap to the distal end of the flap. The flap first layer has a lateral surface and a medial surface. A generally liquid permeable second layer at least partially surrounds the lateral and medial surfaces of the flap first layer, with the flap second layer being free from fixed engagement with at least a portion of the medial surface of the flap first layer to define a surge chamber therebetween for receiving liquid body waste.

In yet another aspect of the present invention, the disposable absorbent article generally comprises a liner adapted for contiguity with the wearer's skin, with at least a portion of the liner being liquid permeable. An outer cover is disposed in opposed relation with the liner. An absorbent body is disposed between the liner and cover sheet for absorbing liquid body waste, with the absorbent body being secured to the liner and being further secured to the outer cover to generally secure the absorbent body against movement relative to the liner and outer cover. The liner is secured to the outer cover about a periphery of the absorbent body to inhibit liquid body waste absorbed by the absorbent body against leaking out of the article between the liner and the outer cover. A pair of containment flaps is secured to the liner in spaced relation with each other. Each containment flap comprises a first layer extending from a base of the flap to a distal end of the flap. At least a portion of the distal end of the flap is spaced from the liner. The flap first layer has a lateral surface and a medial surface. A generally liquid permeable second layer overlays the lateral surface of the flap first layer from the base of the flap to the distal end of the flap and is secured to the lateral surface. The flap second layer extends in opposed relation with the medial surface of the flap first layer from the distal end of the flap to the liner. The flap second layer is secured to the medial surface of the flap first layer at a first seam adjacent the distal end of the flap and is further secured to the liner in laterally inward spaced relation with the base of the flap so that the liner, the flap first layer extending between the seam and the base, and the flap second layer extending between the seam and the liner together form a surge chamber for receiving body waste. An elastic member is secured between the flap first layer and the flap second layer generally at the distal end of the flap to bias the distal end of the flap toward a position in which the flap extends generally transverse to the liner.

Toilet training pants of the present invention generally comprise an anterior side, a posterior side and a crotch region disposed longitudinally therebetween. The anterior side, posterior side and crotch region are integrally formed and are configured to define a central waist opening and a pair of leg openings of the pants, with the crotch region extending generally laterally between the leg openings. An inner layer of the pants extends from the anterior side through the crotch region to the posterior side and is adapted for contiguity with the wearer's skin. At least a portion of the inner layer is liquid permeable. An outer layer extends from the anterior side through the crotch region to the posterior side in opposed relation with the inner layer and an absorbent body is disposed between the inner layer and the outer layer of the pants for absorbing liquid waste. A pair of containment flaps is secured to the inner layer of the pants in laterally spaced relation with each other between the leg openings and extending generally longitudinally from the anterior side through the crotch region to the posterior side of the pants. Each flap has a base secured to the inner layer of the pants and a distal end. At least a portion of the distal end is movable relative to the base to a position in which the flap is spaced from the inner layer of the pants. Each containment flap comprises a first layer extending from the base of the flap to the distal end of the flap. The flap first layer has a lateral surface and a medial surface. A generally liquid permeable second layer is in opposed relation with the medial surface of the flap first layer and is free from fixed engagement with at least a portion of the medial surface of the flap first layer to define a surge chamber therebetween for receiving body waste. The liquid permeable portion of the inner layer of the pants is interposed between the surge chamber and the absorbent body of the pants.

Finally, a method of the present invention for manufacturing toilet training pants comprises securing an absorbent body between a liner and an outer cover and securing the liner to the outer cover about a periphery of the absorbent body. The liner is adapted for contiguity with the wearer's skin and at least a portion of the liner is liquid permeable. The liner and outer cover together define an anterior side, a crotch region and a posterior side of the training pants. Front and rear side panels are secured respectively to the anterior and posterior sides of the training pants to extend laterally outward therefrom. Adjacent front and rear side panels are secured together so that the side panels, together with the anterior side, crotch region and posterior side, form a central waist opening and a pair of leg openings of the training pants, with the crotch region being disposed between the leg openings. A pair of containment flaps is secured to the liner in spaced relation with each other. Each of the flaps is formed by securing a first layer of the flap to the liner to define a base of the flap. A generally liquid permeable second layer is laid over a lateral surface of the flap first layer from the base of the flap to a distal end thereof and is secured to the lateral surface of the flap first layer. The flap second layer is wrapped around the distal end of the flap and overlays the medial surface of the flap first layer from the distal end of the flap to the liner. The flap second layer is secured to the liner in laterally inward spaced relation with the base of the flap so that the liner, the medial surface of the flap first layer extending between the distal end and the base, and the flap second layer extending between the distal end and the liner together form a surge chamber for receiving liquid body waste. An elastic member is secured between the flap first layer and the flap second layer to bias the distal end of the flap to a position in which the distal end is spaced from the liner.

Other aspects and features of this invention will be in part apparent and in part pointed out hereinafter.

BRIEF DESCRIPTION OF THE DRAWINGS

Corresponding reference characters indicate corresponding parts throughout the drawings.

Definitions

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(c) "Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "non-wettable" or hydrophobic.

(d) "Layer" when used in the singular can have the dual meaning of a single element or a plurality of elements.

(e) "Liquid impermeable," when used in describing a layer or multi-layer laminate means that liquid body waste, such as urine, will not pass through the layer or laminate, under ordinary use conditions, in a direction generally perpendicular to the plane of the layer or laminate at the point of liquid contact. Liquid body waste may spread or be transported parallel to the plane of the liquid impermeable layer or laminate, but this is not considered to be within the meaning of "liquid impermeable" when used herein.

(f) "Liquid permeable" refers to any material present in one or more layers which is not liquid impermeable.

(g) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(h) "Non-woven" and "non-woven web" refer to materials and webs of material which are formed without the aid of a textile weaving or knitting process.

(i) "Pliable" refers to materials which are compliant and which will readily conform to the general shape and contours of the wearer's body.

(j) "Spunbond" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

(k) "Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

(l) "Surface" includes any layer, film, woven, nonwoven, laminate, composite, or the like, whether pervious or impervious to air, gas, and/or liquids.

(m) "Surge Layer" refers to a layer typically comprised of nonwoven materials that can absorb a large stream or gush of liquid and release it slowly into another layer or layers.

(n) "Thermoplastic" describes a material that softens when exposed to heat and which substantially returns to a non-softened condition when cooled to room temperature.

(o) "Three dimensional" refers to a garment similar to underwear, shorts or pants in that it has continuous leg and waist openings that are bounded by material of which the garment is made. The garment may or may not have manually tearable or refastenable seams.

DETAILED DESCRIPTION OF THE PREFERRED EMBODIMENTS

Figure 1:
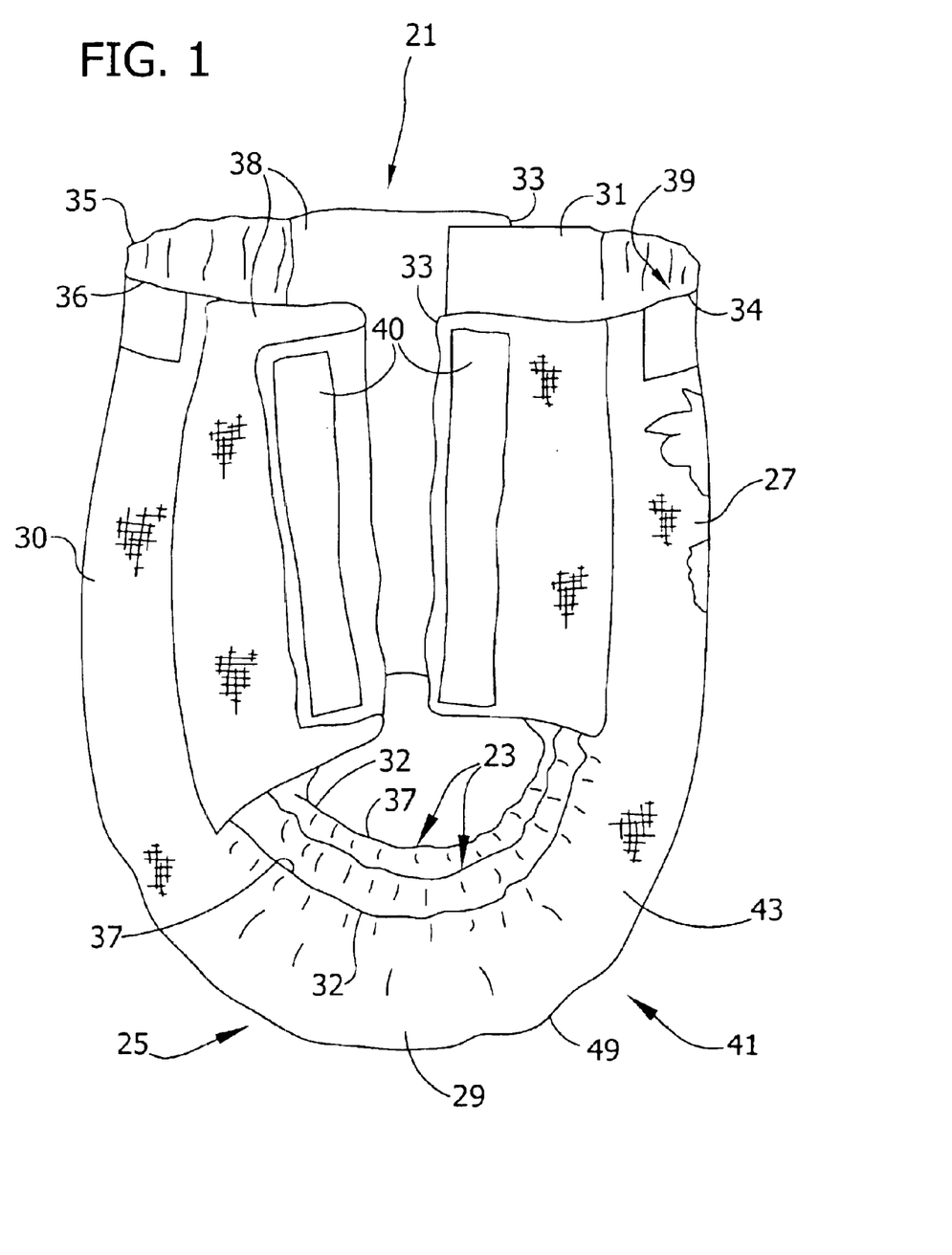
FIG. 1 is a side perspective of a children's toilet training pants incorporating containment flaps of the present invention.

Referring now to the drawings and in particular to FIG. 1, a disposable absorbent article in the form of children's toilet training pants is indicated in its entirety by the reference numeral 21 and incorporates containment flaps, generally indicated at 23, of the present invention for inhibiting leakage of liquid body waste, such as urine, from the training pants. As used herein, a disposable absorbent article refers to articles which may be placed against or in proximity to the body of the wearer to absorb and/or retain various liquid waste discharged from the body. Such articles are intended to be discarded after a limited period of use instead of being laundered or otherwise restored for reuse. While the containment flaps 23 of the present invention are shown and described herein in connection with children's toilet training pants, it is understood that the containment flaps may be incorporated into various other disposable absorbent articles, such as diapers, adult incontinence garments, sanitary napkins and the like, as well as surgical bandages and sponges, without departing from the scope of the present invention.

By way of illustration only, various materials and methods for constructing the training pants 21 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
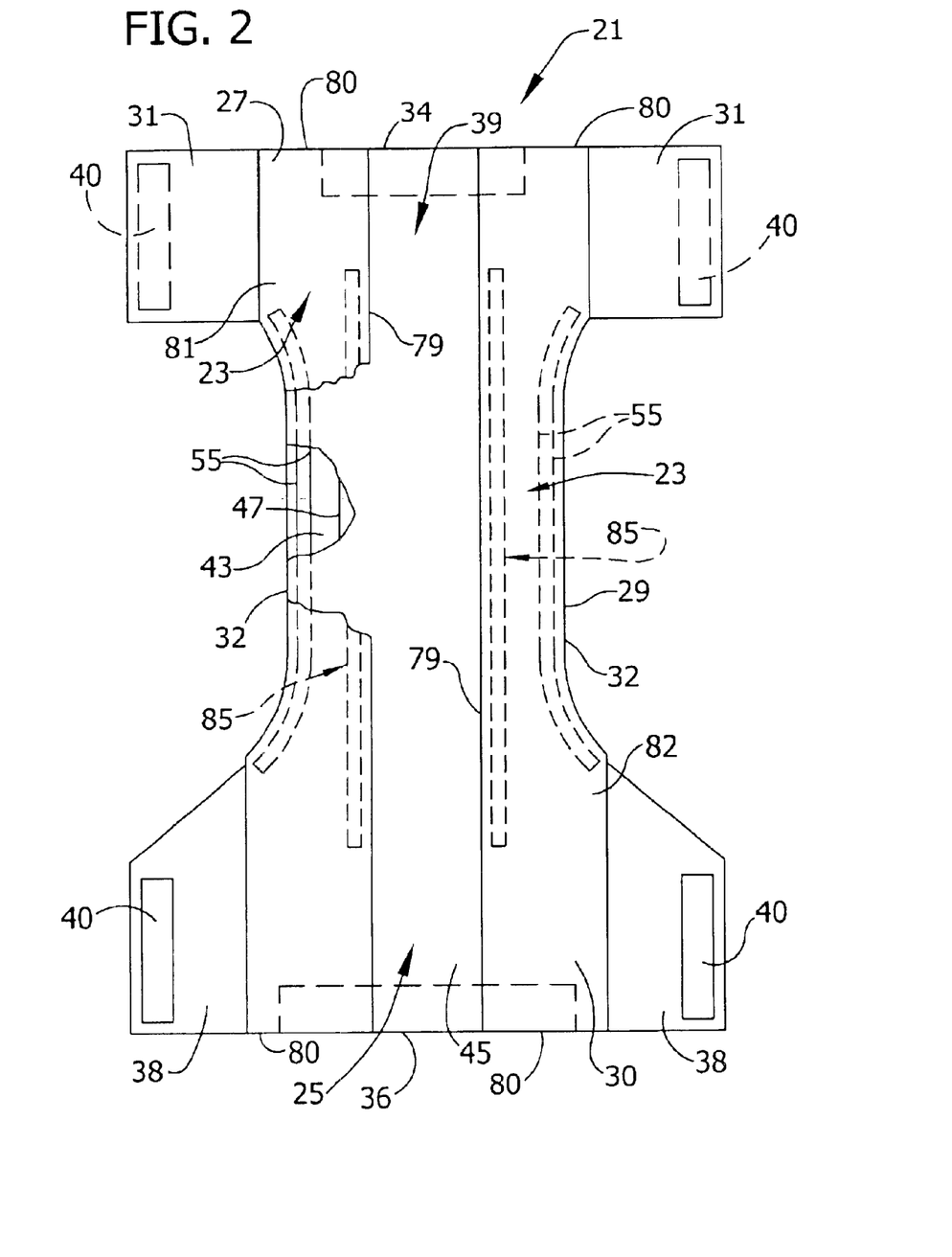
FIG. 2 is a top plan view of the training pants of FIG. 1 with the pants shown unfastened and unfolded.
Figure 3:
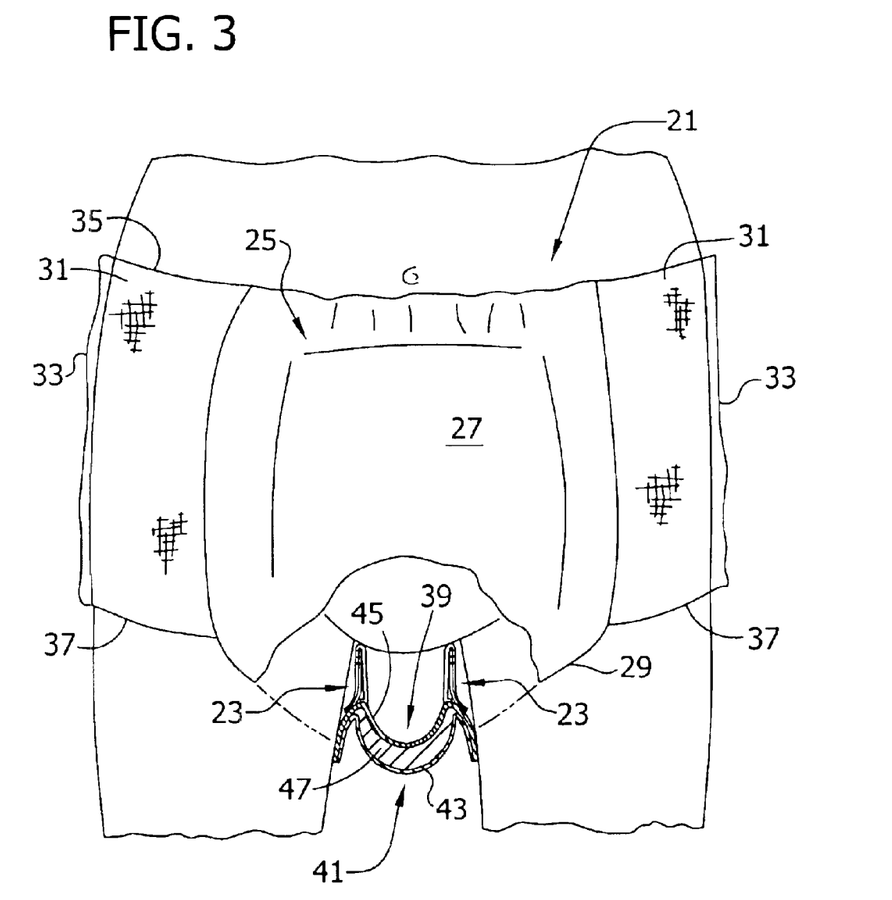
FIG. 3 is a fragmentary front elevation of training pants partially fitted on a child.

The training pants 21 of the illustrated embodiment generally comprise a central absorbent assembly 25 extending longitudinally from an anterior side 27 of the training pants through a crotch region 29 to a posterior side 30 of the training pants. As seen best in FIG. 2, the central absorbent assembly 25 is generally rectangular and has laterally, or transversely opposite side edges 32 and longitudinally opposite front and rear waist edges respectively designated 34 and 36. Front and rear side panels 31, 38 are secured to the central absorbent assembly 25 as will be described later herein and extend laterally outward therefrom respectively at the anterior and posterior sides 27, 30 of the training pants 21. To form the three-dimensional training pants 21, adjacent front and rear side panels 31, 38 (e.g., one extending from the anterior side 27 and one extending from the posterior side 30 on the same right or left side of the pants) are refastenably secured together, using fastening assemblies 40, along generally vertical seams 33 (FIG. 3). It is understood that the front and rear side panels 31, 38 may instead be permanently secured together, such as by ultrasonic bonding. Securing the side panels 31, 38 together defines a central waist opening 35 and a pair of leg openings 37 of the training pants 21.

With reference to FIG. 3, the training pants 21 are worn by inserting the wearer's feet through the waist opening 35 and the respective leg openings 37; grasping the training pants near the waist opening; and then pulling the pants up along the wearer's legs until the crotch region 29 of the training pants fits snugly against the crotch of the wearer. The training pants 21 are illustrated in FIG. 3 as being only partially fitted on the child (i.e., the training pants are pulled less than fully up to the crotch) to better illustrate the containment flaps 23 of the present invention, it being understood that the flaps will actually bend or fold along their length when the pants are pulled fully up to the crotch of the wearer. An inner layer, generally indicated at 39, of the training pant 21 faces the skin of the wearer and is adapted for contiguity (e.g., contact or closely spaced relation) with the wearer's skin upon fitting of the training pants on the wearer. The training pants 21 also have an outer layer, generally indicated at 41, facing away from the wearer's skin.

Figure 4:
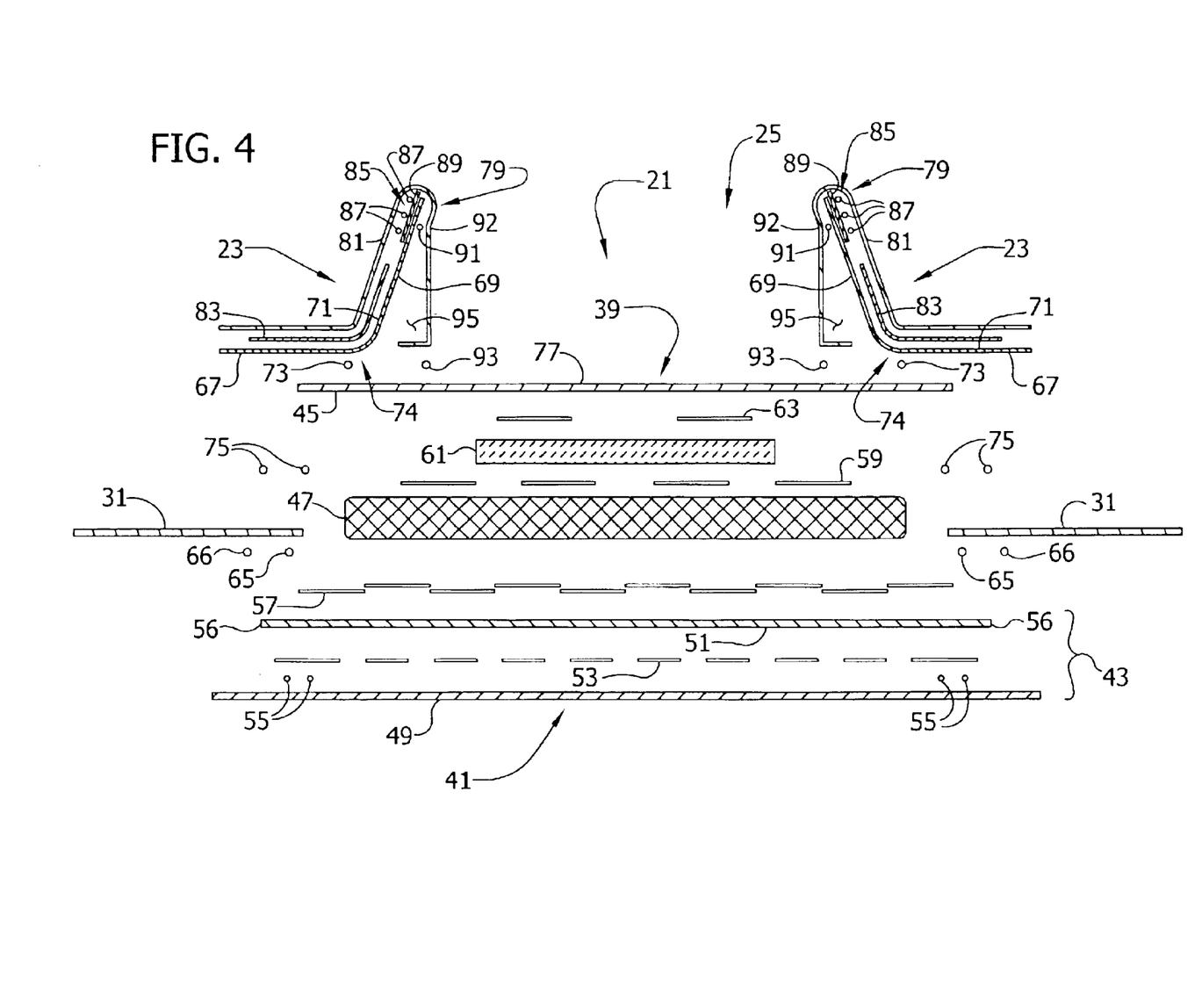
FIG. 4 is a separated cross-section of the training pants of FIG. 1 taken laterally through an anterior side of the pants.

Now referring to FIG. 4, the central absorbent assembly 25 of the training pants 21 comprises an outer cover, generally indicated at 43, a bodyside liner 45 and an absorbent body 47 disposed between the outer cover and the liner. The outer cover 43 can be elastic, stretchable or nonstretchable and is desirably a multi-layered laminate structure of which at least one of the layers is liquid impermeable. For example, the outer cover 43 of the illustrated embodiment is of two-layer construction, including an outer layer 49 constructed of a liquid permeable material and an inner layer 51 constructed of a liquid impermeable material joined together by a laminate adhesive 53. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. It is understood that the outer cover 43 may alternatively be constructed of a single layer of liquid impermeable material without departing from the scope of this invention.

The liquid permeable outer layer 49 of the outer cover 43 can be any suitable material and is desirably one that provides a generally cloth-like texture. One example of such a material is a 20 gsm (grams per square meter) spunbond polypropylene nonwoven web. The outer layer 49 may also be made of those materials from which the bodyside liner 45 is constructed as discussed later herein. Also, while it is not a necessity for the outer layer 49 to be liquid permeable, it is desired that it provide a relatively cloth-like texture to the wearer.

The inner layer 51 of the outer cover 43 can be both liquid and vapor impermeable, or it can be liquid impermeable and vapor permeable. The inner layer 51 is desirably manufactured from a thin plastic film, although other flexible liquid impermeable materials may also be used. The liquid impermeable inner layer 51 (or the liquid impermeable outer cover 43 when the outer cover is constructed of a single layer) inhibits waste material against wetting articles, such as bed sheets and clothing, as well as the wearer and care giver. A suitable liquid impermeable film for such use is a 0.02 millimeter thick polyethylene film commercially available from Huntsman Packaging of Newport News, Va., U.S.A.

Where the outer cover 43 is constructed of a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 43. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Leg elastic members 55 are secured between the outer and inner layers 49, 51 of the outer cover 43, such as by being bonded therebetween by the laminate adhesive 53, generally adjacent laterally outer edges 56 of the inner layer of the outer cover. However, the leg elastic members 55 may instead be disposed between the outer cover 43 and the bodyside liner 45 and remain within the scope of this invention. In such a design, the leg elastic members can be bonded to the outer cover 43 and/or the bodyside liner 45.

A wide variety of elastic materials may be used for the leg elastic members 55. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. For example, one suitable elastic material is a dry-spun coalesced multifilament spandex elastomeric thread sold under the trade name LYCRA® and available from E. I. DuPont de Nemours and Company, Wilmington, Del., U.S.A.

The absorbent body 47 of the illustrated embodiment is somewhat rectangular and is desirably constructed to be generally compressible, pliable, non-irritating to the wearer's skin and capable of absorbing and retaining liquid body waste, such as urine. The absorbent body 47 can be manufactured in a wide variety of sizes and shapes, and from a variety of liquid absorbent materials commonly used in the art. For example, the absorbent body 47 can suitably include a matrix of hydrophilic fibers, such as a web of cellulosic fluff, mixed with particles of a high-absorbency material commonly known as superabsorbent material. More particularly, the absorbent body 47 of the illustrated embodiment includes a matrix of cellulosic fluff, such as wood pulp fluff, and superabsorbent hydrogel-forming particles. One suitable type of wood pulp fluff is identified with the trade designation CR1654, available from U.S. Alliance, Childersburg, Ala., U.S.A., and is a bleached, highly absorbent sulfate wood pulp containing primarily soft wood fibers. However, the wood pulp fluff can be exchanged with synthetic, polymeric, meltblown fibers or with a combination of meltblown fibers and natural fibers.

The superabsorbent particles can be substantially homogeneously mixed with the hydrophilic fibers or can be non-uniformly mixed. The fluff and superabsorbent particles can also be selectively placed into desired zones of the absorbent body 47 to better contain and absorb liquid body waste. The concentration of the superabsorbent particles can also vary through the thickness of the absorbent body 47. Alternatively, the absorbent body 47 can include a laminate of fibrous webs and superabsorbent material or other suitable means of maintaining a superabsorbent material in a localized area. Suitable superabsorbent materials can be selected from natural, synthetic, and modified natural polymers and materials. The superabsorbent materials can be inorganic materials, such as silica gels, or organic compounds, such as cross-linked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

As a general rule, the superabsorbent material is present in the absorbent body 47 in an amount of from about 0 to about 90 weight percent based on total weight of the absorbent body. The absorbent body 47 suitably has a density within the range of about 0.10 to about 0.35 grams per cubic centimeter. The absorbent body 47 may or may not be wrapped or encompassed by a suitable wrapping (not shown) that maintains the integrity and/or shape of the absorbent assembly. As shown in FIG. 4, the absorbent body 47 overlays the inner layer 51 of the outer cover 43, extending laterally between the leg elastic members 55, and is secured to the inner layer 51 of the outer cover 43, such as by being bonded thereto with adhesive 57.

Still referring to FIG. 4, the bodyside liner 45 overlays the absorbent body 47 to isolate the wearer's skin from liquid body waste retained by the absorbent body and is secured to at least a portion of the absorbent body, such as by being bonded thereto using a suitable adhesive 59. The liner 45 further extends beyond the absorbent body 47 to overlay a portion of the inner layer 51 of the outer cover 43, particularly in the crotch region 29 of the pants 21, and is secured thereto, such as by being bonded thereto by the adhesive 57, to substantially enclose the absorbent body between the outer cover and the liner about the periphery of the absorbent body. While the bodyside liner 45 shown in FIG. 4 is dimensioned slightly smaller than the outer cover 43, it is understood that the liner and outer cover may be of the same dimensions, or the liner may be sized larger than the outer cover, without departing from the scope of this invention. The bodyside liner 45 is desirably compliant, soft feeling, and non-irritating to the wearer's skin and can be less hydrophilic than the absorbent body 47 to present a relatively dry surface to the wearer and permit liquid body waste to readily penetrate through its thickness.

The bodyside liner 45 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 45. For example, the bodyside liner 45 can be composed of a meltblown or spunbonded web of polyolefin fibers. The bodyside liner 45 can also be a bonded-carded web composed of natural and/or synthetic fibers. The bodyside liner 45 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 45 or can be selectively applied to particular sections of the liner.

A suitable liquid permeable bodyside liner 45 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 43 and bodyside liner 45 of the central absorbent assembly 25 can include elastomeric materials, it is contemplated that the central absorbent assembly may instead be generally inelastic, wherein the outer cover, the bodyside liner and the absorbent body 47 include materials that are generally non-elastomeric.

A surge layer 61, similar to that disclosed in U.S. Pat. No. 5,562,650, the entire disclosure of which is incorporated herein by reference, lies between the bodyside liner 45 and the absorbent body 47 for quickly absorbing surges of liquid body waste that penetrate the liner, and then slowly releasing the liquid body waste to the absorbent body. One suitable material from which the surge layer 61 can be constructed has a basis weight of about 50 gsm, and includes a through-air-bonded-carded web of a homogenous blend of 60 percent 3 denier bicomponent fiber including a polyester core/polyethylene sheath, commercially available from BASF Corporation, and 40 percent 6 denier polyester fiber, commercially available from Hoechst Celanese Corporation of Portsmouth, Va., U.S.A. The surge layer 61 of the illustrated embodiment is secured to the absorbent body 47, such as by being bonded thereto using the adhesive 59 that secures the liner 45 to the absorbent body. The liner 45 is further secured to the surge layer 61, such as by being bonded thereto using a suitable adhesive 63. It is understood, however, that the surge layer 61 may be omitted altogether, so that the liner 45 lies directly on the absorbent body 47 along the full lateral extent thereof, without departing from the scope of this invention.

The front and rear side panels 31, 38 of the absorbent article 21 can be permanently bonded to the central absorbent assembly 25 of the training pants 21 at the respective anterior and posterior sides 27, 30 thereof. For example, as shown in FIG. 4, the front side panels 31 of the illustrated embodiment are secured to the inner layer 51 of the outer cover 43, such as by being bonded thereto by adhesive 65, or by thermal or ultrasonic bonding, and are also secured to the outer layer 49 of the outer cover, such as by being bonded thereto by additional adhesive 66, or by thermal or ultrasonic bonding, to extend transversely beyond the transverse edges 32 of the central absorbent assembly 25 at the anterior side 27 of the training pants 21 as shown in FIG. 2. The rear side panels 38 are secured to the inner layer 51 and outer cover 43 at the posterior side 30 of the training pants 21 in a similar manner. Alternatively, the side panels 31, 38 can be formed integrally with the central absorbent assembly 25, such as by being formed integrally with the outer cover 43 or the bodyside liner 45.

For improved fit and appearance, the side panels 31, 38 desirably have an average length dimension measured parallel to the longitudinal axis of the training pants 21 that is about 20 percent or greater, and particularly about 25 percent or greater, of the overall length dimension of the training pants, also measured parallel to the longitudinal axis. For example, for training pants 21 having an overall length dimension of about 54 centimeters, the side panels 31, 38 desirably have an average length dimension of about 10 centimeters or greater, such as about 15 centimeters.

Each of the side panels 31, 38 can be constructed of one or more individual, distinct pieces of material. For example, each side panel 31, 38 can include first and second side panel portions (not shown) joined at a seam (not shown), with at least one of the portions including an elastomeric material. Alternatively, each individual side panel 31, 38 can be constructed of a single piece of material folded over upon itself along an intermediate fold line (not shown).

The side panels 31, 38 desirably include an elastic material capable of stretching transversely (e.g., laterally outward) of the training pants 21. Suitable elastic materials, as well as one described process of incorporating elastic side panels into training pants, are described in the following U.S. Pat. No. : 4,940,464 issued Jul. 10, 1990 to Van Gompel et al.; U.S. Pat. No. 5,224,405 issued Jul. 6, 1993 to Pohjola;

U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panels 31, 38 may include other woven or nonwoven materials, such as those described above as being suitable for the outer cover 43 or bodyside liner 45, or stretchable but inelastic materials.

In the illustrated embodiment, the inner layer 39 of the training pants 21 is primarily defined by the liner 45, particularly in the crotch region 29 of the pants. As used herein, the inner layer 39 of the training pants 21 generally refers to that layer of the pants facing the wearer's skin and adapted for contiguity therewith when the training pants are fitted on the wearer's body. It is contemplated that the inner layer 39 of the training pants 21 may be further defined by elements in addition to the liner 45. For example, at the anterior and posterior sides 27, 30 of the training pants 21, the side panels 31, 38 extend laterally outward beyond the liner 45 and contact the wearer's skin, thereby together with the liner 45 defining the inner layer 39 of the training pants. Through the crotch region 29 of the training pants 21, the outer cover 43 extends laterally outward beyond the liner 45, and the side panels 31 do not extend longitudinally through the crotch region, so that the outer cover contacts the wearer's skin, thereby together with the liner defining the inner layer 39. It is also understood that elements other than the side panels 31, 38 or outer cover 43 may overlay, underlie or otherwise extend laterally beyond the liner 45 to face the wearer's skin in contiguity therewith at least partially to define the inner layer 39 of the training pants 21 without departing from the scope of this invention.

The outer layer 41 of the training pants 21 of the illustrated embodiment, facing away from the wearer's skin, is broadly defined by the outer layer 49 of the outer cover 43. It is contemplated, however, that the training pants outer layer 41 may be defined by elements (not shown) other than or in addition to the outer layer 49 of the outer cover 43 without departing from the scope of this invention.

The containment flaps 23 of the present invention are secured to the inner layer 39 (in the illustrated embodiment, the bodyside liner 45) in generally parallel, spaced relation with each other laterally inward of the leg openings 37 and extend longitudinally from the anterior side 27 of the training pants, through the crotch region 29 to the posterior side 30 of the training pants 21. Each containment flap 23 comprises a first, inner layer 67 having medial (e.g., generally inward facing) and lateral (e.g., generally outward facing) surfaces, respectively designated 69 and 71. The flap inner layer 67 is desirably constructed of a liquid impermeable material, but may instead be constructed of a liquid permeable material. A portion of the medial surface 69 of the flap inner layer 67 extends in opposed relation with the bodyside liner 45 and is secured thereto, such as by being bonded thereto by suitable adhesive 73, to broadly define a base, generally indicated at 74, of the flap 23. The base 74 of the flap 23 shown in FIG. 4 extends laterally beyond the liner 45 and is further secured to the side panels 31, 38 at the anterior and posterior sides 27, 30 of the training pants 21, such as by bonding the medial surface 69 of the flap inner layer 67 to the side panels by suitable adhesive 75. While not shown in the drawings, the flap inner layer 67 may be further secured to the inner layer 51 of the outer cover 43 through the crotch region 29 of the training pants 21 to inhibit liquid body waste against flowing out of the training pants between the flap 23 and the outer cover 43. However, it is understood that the flap 23 may be secured only to the bodyside liner 45, or only to the outer cover 43, and remain within the scope of this invention.

The lateral spacing between the respective bases 74 of the containment flaps 23 defines a medial region 77 of the liner 45 extending laterally therebetween, and more particularly between the innermost locations at which the bases are secured to the liner, such as along adhesives 73 securing the inner layers 67 of the flaps to the liner. In the illustrated embodiment the bases 74 of the flaps 23 are secured to the liner 45 generally adjacent the periphery of the absorbent body 47. However, it is understood that the bases 74 of the flaps 23 may be secured to the liner 45 in more closely or more distally spaced relation with each other without departing from the scope of this invention, as long as the bases of the flaps are secured to the liner generally laterally inward of the securement of the liner to the outer cover 43. The flap inner layer 67 further extends from the base 74 to a distal end, generally indicated at 79, of the flap 23. The distal end 79 or other surfaces of the flap 23 can be secured to the liner 45 or to another component of the pants 21 at longitudinal ends 80 (FIG. 2) of the flaps 23. Intermediate the longitudinal ends 80 of each flaps 23, the distal end 79 of the flap 23 is free of fixed engagement with the base 74 of the flap and the liner 45 so that the distal end of the flap is movable relative to the base 74 of the flap and the liner 45 along at least a portion of the flap between the longitudinal ends of the flap.

Each flap 23 further comprises a second, outer layer 81 constructed of a generally liquid permeable material. The flap outer layer 81 overlays substantially the entire lateral surface 71 of the flap inner layer 67 in closely spaced relation therewith and is secured thereto, such as by being bonded thereto by suitable adhesive 83. An elastic member, generally indicated at 85, is secured between the flap outer layer 81 and the lateral surface 71 of the flap inner layer 67 adjacent the distal end 79 of the flap 23. The elastic member 85 of the illustrated embodiment comprises three individual strands 87 of elastomeric material extending longitudinally along the distal end 79 of the flap 23 in generally parallel, spaced relation with each other. One suitable elastic strand 87 is constructed of a LYCRA® T151 940 decitex elastic which can be obtained from E. I. du Pont de Nemours Co. of Wilmington, Del., U.S.A.

The elastic strands 87 are secured between the flap outer layer 81 and the lateral surface 71 of the flap inner layer 67, such as by being bonded therebetween by suitable adhesive 89, in an elastically contractible condition such that contraction of the strands gathers and shortens the distal end 79 of the containment flap 23. As a result, upon folding of the pants 21 to form the three dimensional article, the elastic strands 87 bias the distal end 79 of each flap 23 toward a position spaced from the base 74 of the flap so that in the crotch region 29 of the training pants 21, the flap extends inward from the liner 45 in a generally upright orientation as shown in FIGS. 3 and 4. It is understood that the elastic member 85 may be disposed between the flap outer layer 81 and the flap inner layer 67 other than at the distal end 79 of the flap 23 without departing from the scope of this invention, as long as the elastic member is spaced from the base 74 of the flap. It is also understood that the elastic member 85 may be omitted and the flap may instead be biased toward an upright orientation by elastic materials present in the flap inner and/or outer layers 67, 81. The elastic strands 87 may extend the full length of the flap 23 or they may extend only through a portion of the flap where the flap is desired to be spaced from the liner 45.

Still referring to FIG. 4, the outer layer 81 of each containment flap 23 folds over the flap inner layer 69 at the distal end 79 of the flap and extends in opposed relation with the medial surface 69 of the flap inner layer from the distal end 79 of the flap to the medial region 77 of the liner 45. The flap outer layer 81 of the illustrated embodiment is secured to the medial surface 69 of the flap inner layer 67, such as by being bonded thereto by suitable adhesive 91, generally at the distal end 79 of the flap 23 to broadly define a seam 92 of the flap outer layer to the medial surface of the flap inner layer. However, it is understood that the flap outer layer 81 need not be secured to the medial surface 69 of the flap inner layer 67, so that the adhesive 91 and seam 92 are omitted, and remain within the scope of this invention.

The flap outer layer 81 is further secured to the medial region 77 of the liner 45, such as by being bonded thereto using a suitable adhesive 93, in laterally spaced relation with the base 74 of the flap 23. In the upright orientation of the flap 23, the flap outer layer 81 is generally taut as it extends between the liner 45 and the seam 92 such that the flap outer layer, the portion of the liner between adhesive 73 and the adhesive 93, and the medial surface 69 of the flap inner layer 67 together define a generally triangular, fully enclosed surge chamber 95 for receiving liquid body waste.

In the illustrated embodiment of FIG. 4, the width of the flap outer layer 81 extending between the liner 45 and the seam 92 (or the distal end 79 of the flap 23 if adhesive 91 is omitted) is less than the width of the flap inner layer 67 extending outward from the base 74 of the flap 23 to the seam 92 (or distal end 79) so the flap inner layer is angled transversely and laterally inward relative to the base and the liner 45. It is contemplated that the width of the flap outer layer 81 extending between the liner 45 and the seam 92 may instead be greater than the width of the flap inner layer 67 extending outward from the base 74 to the seam 92 so the flap inner layer extends generally perpendicular to the base, as long as the flap outer layer is spaced from the flap inner layer to form the surge chamber 95. It is also understood that the flap outer layer 81 may be secured to the medial surface 69 of the flap inner layer 67 other than at the distal end 79 of the flap 23, such as anywhere spaced from the base 74 of the flap, or the flap outer layer may not be secured at all to the flap inner layer, without departing from the scope of this invention. As described previously, the surge chamber 95 is partially defined by the portion of the medial region 77 of the liner 45 extending laterally between the adhesive 73 securing the base 74 of the flap 23 to the liner and the adhesive 93 securing the flap outer layer 81 to the liner so that the liner is interposed between the surge chamber and the absorbent body 47 of the training pants 21.

The surge chamber 95 extends longitudinally substantially the length of the flap 23 from the anterior side 27 through the crotch region 29 to the posterior side 30 to permit liquid body waste received in the surge chamber to flow longitudinally therein. To secure the longitudinal ends of the flap 23 to the liner 45, the flap outer layer 81 between the adhesive 93 and the distal end 79 of the flap 23 can be secured to the liner 45, such as with adhesive (not shown) or other suitable fastening, generally at the longitudinal ends 80 of the flap to thereby close off the surge chamber 95 against flow longitudinally outward therethrough.

The flap outer layer 81 can be constructed of a spunbond polypropylene non-woven web and the flap inner layer 67 can be constructed of a polyethylene film to severely retard the flow of liquid body waste outward of the flap 23. However, it is contemplated that the flap inner layer 67 may be constructed other than of a film or other liquid impermeable material. For example, the flap inner layer 67 may instead be constructed of one or more layers of a liquid permeable material, and the liquid permeable material may be treated to decrease the permeability thereof. It is also contemplated that the flap outer layer 81 can be constructed of other liquid permeable materials, such as a polyethylene or polypropylene film having apertures formed therein to permit liquid body waste to flow therethrough to the surge chamber 95. Since the bodyside liner 45 is liquid permeable, the surge chamber 95 is generally in fluid communication with the absorbent body 47 to permit liquid body waste received in the surge chamber to pass through the liner for absorption by the absorbent body. When a surge of liquid body waste flows laterally outward along the medial region 77 of the liner 45, it flows outward against the portion of the flap outer layer 81 defining the surge chamber 95 and passes through the flap outer layer into the surge chamber 95. The flap inner layer 67 inhibits liquid body waste received in the surge chamber 95 against flowing laterally outward beyond the containment flap 23. As a result, liquid body waste accumulates within the surge chamber 95 during the liquid surge, and is temporarily retained therein until the liquid body waist can pass through the medial region 77 of the liner 45 interposed between the surge chamber and the absorbent body for absorption by the absorbent body 47.

While the flap outer layer 81 is shown and described herein as being constructed separate from the liner 45, it is contemplated that the flap outer layer may be secured to liner by being formed integrally therewith, as long as the liner is interposed between the absorbent body 47 and the surge chamber 95 formed by the flap outer layer and the medial surface 69 of the flap inner layer 67. For example, the liner 45 may comprise at least two sheets (not shown) of material, with the liquid impermeable flap inner layer 67 being disposed between the two sheets and secured to a bottom sheet to form the base of the flap 23 and to the top sheet to form the distal end of the flap. While not shown in the drawings, the flap inner layer 67 and/or the flap outer layer 81 may also extend transversely outward over the side panels 31, 38 of the training pants 21, and to the respective side edges 32 of the central absorbent assembly 25 of the pants, without departing from the scope of this invention.

Figure 5:
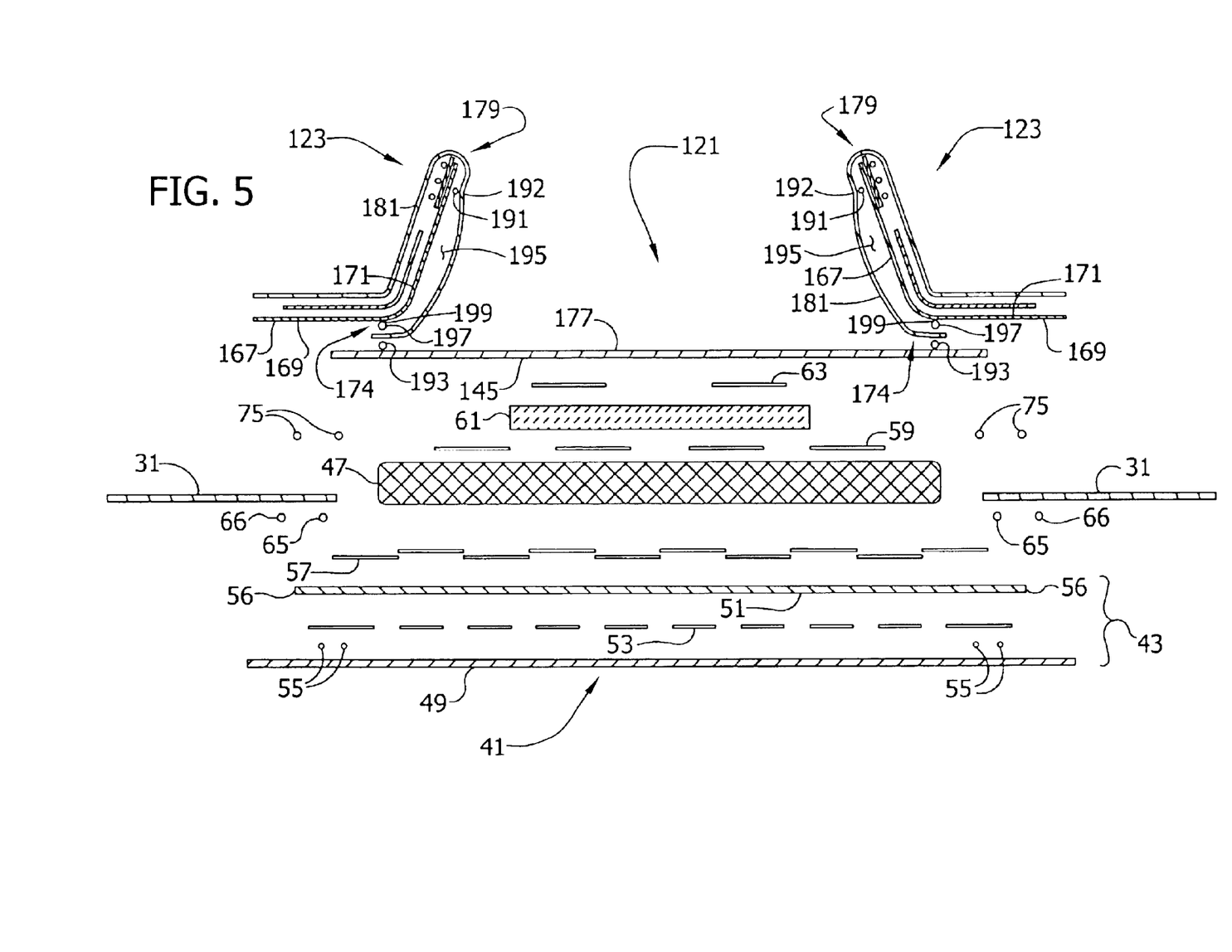
FIG. 5 is a separated cross-section similar to that of FIG. 4 showing a second embodiment of the containment flaps of the present invention.

FIG. 5 illustrates training pants 121 incorporating containment flaps 123 of a second embodiment of the present invention. The containment flaps 123 are substantially similar to those shown in the embodiment of FIGS. 1–4, including a flap inner layer 167 having medial and lateral surfaces 169, 171, and an outer layer 181. The flap outer layer 181 extends in opposed relation with the medial surface 169 of the flap inner layer 167 and is secured thereto, such as by a suitable adhesive 191, to define a seam 192 between the flap outer layer and the medial surface of the flap inner layer generally at the distal end 179 of the flap 123. However, as with the first embodiment, the flap outer layer 181 need not be secured to the medial surface 169 of the flap inner layer 167 at the distal end 179 of the flap 123, so that the adhesive 191 and seam 192 may be omitted.

Instead of the flap outer layer 81 being secured to the liner 45 in laterally spaced relation with the base 74 of the flap 23 as in the first embodiment, the flap outer layer 181 of this second embodiment is secured to the liner 145 generally at the base 174 of the flap 123. More particularly, the flap outer layer 181 is tucked between the liner 145 and the medial surface 169 of the flap inner layer 167 at the base 174 of the flap 123 and is secured to the liner and the flap inner layer, such as by being bonded thereto by respective suitable adhesives 193, 197 to broadly define a second seam 199 of the flap outer layer and the medial surface of the flap inner layer. Alternatively, adhesive 197 securing the flap outer layer 181 to the medial surface of the flap inner layer 167 may be omitted without departing from the scope of this invention.

The flap outer layer 181 is otherwise free from fixed engagement with the medial surface 169 of the flap inner layer 167, and in particular between the seam 192 and the seam 199. The width of the portion of the flap outer layer 181 extending between the seams 192, 199 is substantially greater than the width of the flap inner layer, as shown in FIG. 5, or at least about equal thereto, so that this portion of the flap outer layer hangs generally loosely down along in the medial surface 169 of the flap inner layer 167 between the seams 192, 199 to define a surge chamber 195 between this portion of the flap outer layer and the medial surface of the flap inner layer for receiving liquid body waste.

As in the first embodiment, the medial region 177 of the liner 145 is interposed between the surge chamber 195 and the absorbent body 147 of the training pants 121 of this second embodiment. As a result, when a surge of liquid body waste is received in the surge chamber 195, the liquid waste is temporarily retained therein until the liquid can flow back through the flap outer layer and through the medial region 177 of the liner 145 interposed between the surge chamber and the absorbent body 147 for absorption by the absorbent body.

It is contemplated that the flap outer layer 181 may be secured to the medial surface 169 of the flap inner layer 167 other than at the distal end 179 of the flap 123 so that the seam 192 is spaced from the distal end of the flap, and/or the flap outer layer may be further secured to the medial surface of the flap inner layer other than at the base 174 of the flap so that the seam 199 is spaced from the base, as long as the portions of the flap outer layer and flap inner layer extending between the seams 192, 199 are sized relative to each other so the flap outer layer and flap inner layer define the surge chamber 195 therebetween.

In view of the above, it will be seen that the several objects of the invention are achieved and other advantageous results attained. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent article for personal wear, said disposable absorbent article comprising:
an inner layer adapted for contiguity with the wearer's skin, at least a portion of said inner layer being liquid permeable;
an outer layer in opposed relation with the inner layer;
an absorbent body disposed between the inner layer and the outer layer of said article for absorbing liquid body waste; and
a pair of containment flaps on said article in spaced relation with each other, each flap having a base secured to the article and a distal end, at least a portion of the distal end being movable relative to said base to a position in which said distal end is spaced from the inner layer of said article, said containment flaps each comprising:
a first layer extending from the base of the flap to the distal end of said flap, said flap first layer having a lateral surface, a medial surface; and
a liquid permeable second layer in opposed relation with the medial surface of the flap first layer, said flap second layer being free from fixed engagement with at least a portion of the medial surface of said flap first layer to define a surge chamber therebetween for receiving liquid body waste, the flap second layer having a width greater than a width of said portion of the medial surface of the flap first layer and being secured to at least one of the flap first layer and the inner layer of the article whereby the absorbent body and liquid permeable portion of the inner layer of said article are at least in part disposed between the surge chamber and the outer layer of said article.

2. A disposable absorbent article as set forth in claim 1 wherein said portion of the medial surface of the flap first layer extends substantially from the base of the flap to the distal end of the flap.

3. A disposable absorbent article as set forth in claim 1 wherein the flap second layer is secured to the medial surface of the flap first layer at a first seam therebetween generally at the distal end of the flap.

4. A disposable absorbent article as set forth in claim 1 wherein said portion of the medial surface of the flap first layer extends from the base of the flap generally to the distal end of said flap, said flap second layer extending generally from the distal end of said flap to the inner layer of said article in spaced relation with said portion of the medial surface of the flap first layer to define the surge chamber therebetween, the inner layer of said article further defining said surge chamber.

5. A disposable absorbent article as set forth in claim 4 wherein the flap second layer is secured to the inner layer of said article in spaced relation with the flap first layer.

6. A disposable absorbent article as set forth in claim 4 wherein the surge chamber has a generally triangular cross-section.

7. A disposable absorbent article as set forth in claim 1 wherein the flap second layer is secured to the medial surface of the flap first layer in spaced relation with the base of the flap to define a seam between the flap second layer and the medial surface of said flap first layer, said portion of the medial surface of the flap first layer extending between the base of the flap and said seam, the flap second layer extending between the inner layer of said article and said seam in spaced relation with said portion of the medial surface of the flap first layer to define the surge chamber therebetween, the inner layer of said article further defining said surge chamber.

8. A disposable absorbent article as set forth in claim 7 wherein the flap second layer is secured to the flap first layer generally at the distal end of the flap to define said seam, said flap second layer being further secured to the inner layer of said article in spaced relation with said flap first layer.

9. A disposable absorbent article as set forth in claim 7 wherein the surge chamber has a generally triangular cross-section.

10. A disposable absorbent article as set forth in claim 1 wherein the flap second layer is constructed of a non-woven material.

11. A disposable absorbent article as set forth in claim 10 wherein the flap second layer is constructed of a spunbond polypropylene non-woven web.

12. A disposable absorbent article as set forth in claim 1 wherein the flap second layer is constructed of a film, at least a portion of said film having apertures formed therein.

13. A disposable absorbent article as set forth in claim 1 wherein the flap first layer is substantially liquid impermeable.

14. A disposable absorbent article as set forth in claim 1 wherein each containment flap further comprises an elastic member to bias the distal end of the flap toward a position spaced from the base of the flap.

15. An absorbent article as set forth in claim 1 wherein the absorbent article comprises a pair of training pants having an anterior side, a posterior side and a crotch region disposed longitudinally therebetween, said anterior side, posterior side and crotch region being integrally formed and configured to define a central waist opening and a pair of leg openings of the pants, the crotch region extending generally laterally between said leg openings, the inner layer of the article extending from the anterior side through the crotch region to the posterior side, the outer layer extending from the anterior side through the crotch region to the posterior side in opposed relation with the inner layer, the containment flaps being secured to the inner layer of said pants in laterally spaced relation with each other between the leg openings and extending generally longitudinally from the anterior side through the crotch region to the posterior side of the pants.

16. Toilet training pants as set forth in claim 15 wherein the flap first layer is substantially liquid impermeable.

17. Toilet training pants as set forth in claim 15 wherein each containment flap further comprises an elastic member to bias the distal end of the flap toward a position spaced from the base of the flap.

18. A disposable absorbent article for personal wear, said disposable absorbent article comprising:

an inner layer adapted for contiguity with the wearer's skin, at least a portion of said inner layer being liquid permeable;

an outer layer in opposed relation with the inner layer;

an absorbent body disposed between the inner layer and the outer layer of said article for absorbing liquid body waste; and a pair of containment flaps secured to the article in spaced relation with each other, each flap having a base secured to said article and a distal end, at least a portion of the distal end being movable relative to said base to a position in which said distal end is spaced from the inner layer of said article, said containment flaps each comprising:

a first layer extending from the base of the flap to the distal end of said flap, said flap first layer having a lateral surface and a medial surface; and a liquid permeable second layer in opposed relation with the medial surface of the flap first layer, said flap second layer being free from fixed engagement with at least a portion of the medial surface of said flap first layer to define a surge chamber therebetween for receiving liquid body waste, said flap second layer being secured to the medial surface at a first seam therebetween generally at the distal end of the flap and being further secured to the medial surface at a second seam spaced from said first seam, said portion of the medial surface of the flap first layer extending between the first seam and the second seam, said liquid permeable portion of the inner layer of said article being interposed between the surge chamber and the absorbent body of said article.

19. A disposable absorbent article as set forth in claim 18 wherein said second seam is located generally at the base of the flap.

20. A disposable absorbent article as set forth in claim 18 wherein the flap second layer is tucked between the medial surface of the flap first layer and the inner layer of said article generally at said second seam, said flap second layer being secured to the inner layer of said article thereby securing the base of the flap to the inner layer of said article.

21. A disposable absorbent article for personal wear, said disposable absorbent article comprising:

an inner layer adapted for contiguity with the wearer's skin, at least a portion of said inner layer being liquid permeable;

an outer layer in opposed relation with the inner layer of said article;

an absorbent body disposed between the inner layer and the outer layer of said article for absorbing liquid body waste; and a pair of containment flaps secured to the inner layer of said article in spaced relation with each other, each flap having a base secured to the inner layer of said article and a distal end, at least a portion of the distal arid being movable relative to said base to a position in which the flap is spaced from the inner layer of said article, said containment flaps each comprising:

a first layer extending from the base of the flap to the distal end of said flap, said flap first layer having a lateral surface and a medial surface; and a liquid permeable second layer at least partially surrounding the lateral and medial surfaces of the flap first layer, said flap second layer being free from fixed engagement with at least a portion of the medial surface of said flap first layer to define a surge chamber therebetween for receiving liquid body waste, the absorbent body and liquid permeable portion of the inner layer of said article being at least in part disposed between the surge chamber and the outer layer of said article.

22. A disposable absorbent article as set forth in claim 21 wherein the flap first layer is formed separate from the inner layer of said article.

23. A disposable absorbent article as set forth in claim 21 wherein the flap second layer is formed separate from the inner layer of said article.

24. A disposable absorbent article as set forth in claim 21 wherein the flap second layer inhibits contact of the flap first layer with the wearer's skin.

25. A disposable absorbent article as set forth in claim 24 wherein the flap second layer overlays substantially the entire lateral surface of the flap first layer.

26. A disposable absorbent article as set forth in claim 21 wherein the flap first layer is substantially liquid impermeable.

27. A disposable absorbent article as set forth in claim 21 wherein each containment flap further comprises an elastic member to bias the distal end of the flap toward a position spaced from the base of the flap.

28. A disposable absorbent article for personal wear, said disposable absorbent article comprising:

a liner adapted for contiguity with the wearer's skin, at least a portion of said liner being liquid permeable;

an outer cover in opposed relation with the liner;

an absorbent body disposed between the liner and outer cover for absorbing liquid body waste, the absorbent body being secured to the liner and being further secured to the outer cover to generally secure the absorbent body against movement relative to the liner and outer cover, the liner being secured to the outer cover about a periphery of the absorbent body to inhibit liquid body waste absorbed by the absorbent body against leaking out of the article between the liner and the outer cover; and a pair of containment flaps secured to the liner in spaced relation with each other, each of said flaps comprising:

a first layer extending from a base of the flap adjacent the liner to a distal end of the flap, at least a portion of the distal end of the flap being spaced from the liner, said flap first layer having a lateral surface and a medial surface;

a liquid permeable second layer overlaying the lateral surface of the flap first layer from the base of the flap to the distal end of the flap and being secured to said lateral surface, the flap second layer extending in opposed relation with the medial surface of the flap first layer from the distal end of the flap to the liner, the flap second layer being secured to the medial surface of the flap first layer at a first seam adjacent the distal end of the flap and being further secured to the liner in laterally inward spaced relation with the base of the flap so that the liner, the flap first layer extending between the seam and the base, and the flap second layer extending between the seam and the liner together form a surge chamber for receiving liquid body waste; and an elastic member secured between the flap first layer and the flap second layer generally at the distal end of the flap to bias the distal end of the flap toward a position in which the flap extends from the liner.

29. A disposable absorbent article as set forth in claim 28 wherein the flap first layer is substantially liquid impermeable.

30. An absorbent article as set forth in claim 28 wherein the absorbent body and liquid permeable portion of the liner of said article are at least in part disposed between the surge chamber and the outer cover of said article.

31. A method of manufacturing toilet training pants comprising:

securing an absorbent body between a liner and an outer cover and securing the liner to the outer cover about a periphery of the absorbent body, the liner being adapted for contiguity with the wearer's skin and at least in part being liquid permeable, said liner and outer cover together defining an anterior side, a crotch region and a posterior side of the training pants;

securing front and rear side panels respectively to the anterior and posterior sides of the training pants to extend laterally outward from the liner and outer cover, and securing adjacent front and rear side panels together so that the side panels, together with the anterior side, crotch region and posterior side of the pants form a central waist opening and a pair of leg openings of the training pants, the crotch region being disposed between the leg openings;

securing a pair of containment flaps to the liner in spaced relation with each other, each of said flaps being formed by:

securing a first layer of the flap to the liner to define a base of the flap;

overlaying a liquid permeable second layer over a lateral surface of the flap first layer from the base of the flap to a distal end thereof;

securing said flap second layer to the lateral surface of the flap first layer;

wrapping the flap second layer around the distal end of the flap;

overlaying the flap second layer over a medial surface of the flap first layer from the distal end of the flap to the liner;

securing the flap second layer to the liner in laterally inward spaced relation with the base of the flap so that the liner, the medial surface of the flap first layer extending between the distal end of the flap and the base, and the flap second layer extending between the distal end of the flap and the liner together form a surge chamber for receiving liquid body waste, the absorbent body and liner being at least in part disposed between the surge chamber and the outer cover; and securing an elastic member between the flap first layer and the flap second layer to bias the distal end of the flap to a position in which the distal end is spaced from the liner.

32. A method as set forth in claim 31 further comprising the step of securing the flap second layer to the medial surface of the flap first layer at a first seam spaced from the base of the flap, the step of securing the flap second layer to the liner comprising securing the flap second layer to the liner in laterally inward spaced relation with the base of the flap so that the liner, the medial surface of the flap first layer extending between the seam and the base, and the flap second layer extending between the seam and the liner together form a surge chamber for receiving liquid body waste.

33. A method am set forth in claim 31 wherein the step of securing an elastic member between the flap first layer and the flap second layer comprises securing an elastic member between the flap first layer and the flap second layer generally at the distal end of the flap to bias the distal end of the flap so that the flap extends from the liner in space relation thereto.

34. A disposable absorbent article for personal wear, said disposable absorbent article comprising:

an inner layer adapted for contiguity with the wearer's skin, at least a portion of said inner layer being liquid permeable;

an outer layer in opposed relation with the inner layer;

an absorbent body disposed between the inner layer and the outer layer of said article for absorbing liquid body waste; and a pair of containment flaps secured to the article in spaced relation with each other, each flap having a base secured to said article and a distal end, at least a portion of the distal end being movable relative to said base to a position in which said distal end is spaced from the inner layer of said article, said containment flaps each comprising:

a first layer extending from the base of the flap to the distal end of said flap, said flap first layer having a lateral surface and a medial surface; and a liquid permeable second layer in opposed relation with the medial surface of the flap first layer, said flap second layer being free from fixed engagement with at least a portion of the medial surface of said flap first layer to define a surge chamber therebetween for receiving liquid body waste, said flap second layer also being secured to the medial surface at least at one location therebetween, the flap second layer further extending in opposed relationship with at least a portion of the lateral surface of the flap first layer intermediate the base of the flap and the distal end of the flap and being secured to the lateral surface of the flap first layer at least at one location therebetween.

35. A disposable absorbent article as set forth in claim 34 wherein the flap second layer overlays substantially the entire lateral surface of the flap first layer.

36. An absorbent article as set forth in claim 34 wherein the absorbent body and liquid permeable portion of the liner of said article are at least in part disposed between the surge chamber and the outer cover of said article.

* * * * *